United States Patent
Banipal et al.

(10) Patent No.: US 11,907,273 B2
(45) Date of Patent: Feb. 20, 2024

(54) AUGMENTING USER RESPONSES TO QUERIES

(71) Applicant: International Business Machines Corporation, Armonk, NY (US)

(72) Inventors: Indervir Singh Banipal, Austin, TX (US); Shikhar Kwatra, San Jose, CA (US); Nadiya Kochura, Bolton, MA (US); Sourav Mazumder, Contra Costa, CA (US)

(73) Assignee: International Business Machines Corporation, Armonk, NY (US)

( * ) Notice: Subject to any disclaimer, the term of this patent is extended or adjusted under 35 U.S.C. 154(b) by 73 days.

(21) Appl. No.: 17/351,316

(22) Filed: Jun. 18, 2021

(65) Prior Publication Data
US 2022/0405313 A1 Dec. 22, 2022

(51) Int. Cl.
G06F 17/00 (2019.01)
G06F 16/332 (2019.01)
G06F 16/33 (2019.01)
G06N 5/04 (2023.01)
G06N 20/00 (2019.01)
G06N 5/02 (2023.01)

(52) U.S. Cl.
CPC ...... G06F 16/3329 (2019.01); G06F 16/3344 (2019.01); G06N 5/02 (2013.01); G06N 5/04 (2013.01); G06N 20/00 (2019.01)

(58) Field of Classification Search
CPC ... G06F 16/3329; G06F 16/3344; G06N 5/02; G06N 5/04; G06N 20/00; G06N 5/01; G06N 5/022; G06N 3/0442; G06N 3/0455; G06N 3/0464; G06N 3/047; G06N 3/0475; G06N 3/084; G16H 30/20; G16H 30/40; G16H 40/63; G16H 40/67; G16H 50/20; G16H 50/30; G16H 50/70
See application file for complete search history.

(56) References Cited

U.S. PATENT DOCUMENTS 6,270,456 B1  8/2001  Iliff
7,346,663 B2  3/2008  Abbott
(Continued)

FOREIGN PATENT DOCUMENTS

| CN | 110313153 A | 10/2019 |
| CN | 106716295 B | 5/2020 |
| KR | 20160108051 A | 9/2016 |

OTHER PUBLICATIONS

Simon Keizer and Harry Bunt. 2009. Multidimensional dialogue management. In Proceedings of the 7th SIGdial Workshop on Discourse and Dialogue (SigDIAL '06). Association for Computational Linguistics, USA, 37-45. (Year: 2009).*

(Continued)

*Primary Examiner* — Greta L Robinson
(74) *Attorney, Agent, or Firm* — David K. Mattheis

(57) ABSTRACT

Generating a query response by receiving data for a non-user utterance, determining a question answering (QA) system response to the non-user utterance, receiving data for a user utterance responsive to the non-user utterance, determining a confidence score for the user utterance, determining a deviation between the user utterance and the QA system response, and providing the QA system response according to a combination of the deviation and the confidence score.

18 Claims, 4 Drawing Sheets

(56) References Cited

U.S. PATENT DOCUMENTS

| | | | |
|---|---|---|---|
| 8,165,518 | B2 | 4/2012 | Smith |
| 8,805,756 | B2 | 8/2014 | Boss |
| 9,775,520 | B2 | 10/2017 | Tran |
| 10,489,393 | B1* | 11/2019 | Mittal ................. G06F 16/2455 |
| 10,755,182 | B2* | 8/2020 | Allen ....................... G06N 5/04 |
| 10,854,191 | B1 | 12/2020 | Geramifard |
| 10,950,223 | B2* | 3/2021 | Debnath ................ G06F 40/30 |
| 10,978,056 | B1 | 4/2021 | Challa |
| 11,373,640 | B1* | 6/2022 | Chen ..................... H04L 41/145 |
| 2014/0099614 | A1 | 4/2014 | Hu |
| 2014/0310295 | A1 | 10/2014 | Stivoric |
| 2016/0026378 | A1 | 1/2016 | Isensee |
| 2017/0249434 | A1 | 8/2017 | Brunner |
| 2018/0082032 | A1 | 3/2018 | Allen |
| 2018/0358001 | A1* | 12/2018 | Amid ................... G06F 16/3329 |
| 2020/0342850 | A1* | 10/2020 | Vishnoi ................. H04L 51/214 |

OTHER PUBLICATIONS

"Adapting Conversation Based on Perceived User Expertise", IP.com No. IPCOM000258019D, IP.com Electronic Publication Date: Apr. 1, 2019, 5 pps.

"Logistic regression", From Wikipedia, the free encyclopedia, last edited on May 22, 2021, 17 pps., <https://en.wikipedia.org/wiki/Logistic_regression>.

"Method and System for Improving Fidelity of Dynamically Retrieved Answers via Conversational Unsupervised Learning", IP.com No. IPCOM000256532D, IP.com Electronic Publication Date: Dec. 6, 2018, 4 pps.

"Method and System for Voluntarily Inserting an Unsolicited Response in Human Conversations", IP.com No. IPCOM000256314D, IP.com Electronic Publication Date: Nov. 17, 2018, 5 pps.

"Method to Reduce the Number of Questions Asked Due to Conversation Handoffs Between Agents", IP.com No. IPCOM000265556D, IP.com Electronic Publication Date: Apr. 23, 2021, 5 pps.

"Questions Your Doctor May Ask", National Jewish Health, © 2021 National Jewish Health, 2 pps., <https://www.nationaljewish.org/patients-visitors/patient-info/prepare-for-your-appointment/doctor-may-ask>.

"Statistical hypothesis testing", From Wikipedia, the free encyclopedia, last edited on Jun. 4, 2021, 10 pps., <https://en.wikipedia.org/wiki/Statistical_hypothesis_testing>.

"Use advanced NLP and tone analysis to extract meaningful insights", © 2021 GitHub, Inc., 8 pps., <https://github.com/IBM/use-advanced-nlp-and-tone-analyser-to-analyse-speaker-insights>.

"Watson Natural Language Understanding", IBM, downloaded from the Internet on Jun. 15, 2021, 4 pp., <https://www.ibm.com/watson/services/personality-insights/>.

Abbasiantaeb et al., "Text-based Question Answering from Information Retrieval and Deep Neural Network Perspectives: A Survey", Submitted on Feb. 16, 2020 (v1), last revised May 27, 2020 (this version, v2), 56 pps, Cornell University, <https://arxiv.org/abs/2002.06612>.

Alegre, "The Enhancement of Pragmatic Competencies via Listening Activities", Thesis, aculdade de Letras da Pontifícia Universidade Católica do Rio Grande do Sul, 2009, 207 pps.

Aqle et al., "Analyze Unstructured Data Patterns for Conceptual Representation", downloaded from the Internet on Jun. 16, 2021, 4 pps., <https://arxiv.org/pdf/1808.10259.pdf>.

Bitzioinis, "Covidentify Study Looks to Smartphone, Wearable Biometrics for Symptoms of COVID-19", Apr. 9, 2020, Findbiometrics, 4 pps., <https://findbiometrics.com/covidentify-smartphones-wearables-biometrics-early-symptoms-covid-19-040901/>.

Burnham, "Model Selection and Multimodal Inference", A Practical Information-Theoretic Approach, Second Edition, @ 1998, 515 pps., <https://archive.org/details/modelselectionmu0000burn>. (Relevant Information pp. 122-132 and Chapter 4).

Dalmas et al., "Answer comparison in automated question answering", Journal of Applied Logic 5 (2007) 104-120, Science Direct, <https://www.sciencedirect.com/science/article/pii/S1570868305000947>.

Edlund et al., "Pause and ggaap length in face-to-face interaction", 4 pps., dowloaded from the Internet on Jun. 16, 2021, <http://www.cs.columbia.edu/nlp/papers/2009/edlund_al_09.pdf>.

Ekman, "Micro Expressions", Copyright © 2021 Paul Ekman Group LLC. All rights reserved, 4 pps., <https://www.paulekman.com/resources/micro-expressions/>.

Fawaz et al., "Deep Neural Network Ensembles for Time Series Classification", last revised Apr. 26, 2019, 6 pps., <https://arxiv.org/abs/1903.06602>.

Fierro et al., "Predicting Unplanned Readmissions with Highly Unstructured Data", arXiv:2003.11622v2 [cs.CL] Apr. 5, 2020, Accepted as a workshop paper at AI4AH, ICLR 2020, 7 pps., <https://arxiv.org/abs/2003.11622>.

Geller, "Normalization vs Standardization—Quantitative analysis", Apr. 4, 2019, 17 pps., <https://towardsdatascience.com/normalization-vs-standardization-quantitative-analysis-a91e8a79cebf>.

Guk et al., "Evolution of Wearable Devices with Real-Time Disease Monitoring for Personalized Healthcare", Nanomaterials (Basel). Jun. 2019; 9(6): 813, Published online May 29, 2019, doi:10.3390/nano9060813, 19 pps., <https://www.ncbi.nlm.nih.gov/pmc/articles/PMC6631918/>.

Hu et al., "Read + Verify: Machine Reading Comprehension with Unanswerable Questions", Copyright 2019, Association for the Advancement of Artificial Intelligence, arXiv:1808.05759v5 [cs.CL] Nov. 15, 2018, 9 pps., <https://arxiv.org/pdf/1808.05759.pdf>.

Indurthi et al., "Generating Natural language Question—Answer Pairs from a Knowledge Graph Using a RNN Based Question Generation Model", Proceedings of the 15th Conference of the European Chapter of the Association for Computational Linguistics: vol. 1, Long Papers, pp. 376-385, Valencia, Spain, Apr. 3-7, 2017. c 2017 Association for Computational Linguistics, <https://www.aclweb.org/anthology/E17-1036/>.

Jahgirdar et al., "Use advanced natural language processing and tone analysis to extract meaningful insights", Published Jul. 20, 2020, 3 pps., <https://developer.ibm.com/technologies/artificial-intelligence/patterns/use-advanced-nlp-and-tone-analyser-to-extract-insights-from-text/>.

Jaitley, "Why Data Normalization is necessary for Machine Learning models", Medium, Oct. 7, 2018, 5 pps., <https://medium.com/@urvashilluniya/why-data-normalization-is-necessary-for-machine-learning-models-681b65a05029>.

Kim, "Multiple-concept feature generative models for multi-label image classification", Computer Vision and Image Understanding, vol. 136, Jul. 2015, pp. 69-78, <https://www.sciencedirect.com/science/article/pii/S1077314214002239>.

Li et al., "Towards Reading Hidden Emotions: A Comparative Study of Spontaneous Micro-expression Spotting and Recognition Methods", arXiv:1511.00423v2 [cs.CV], Feb. 8, 2017, 14 pps., <https://arxiv.org/abs/1511.00423>.

Mack, "CLEVR graph: A dataset for graph based reasoning", Jun. 11, 2018, Octavian | Medium, 3 pps., <https://medium.com/octavian-ai/clevr-graph-a-dataset-for-graph-based-reasoning-5e4e64f28ffb>.

Mazaheri et al., "Learning a Multi-Concept Video Retrieval Model with Multiple Latent Variables", Published 2018 Computer Science, ACM Transactions on Multimedia Computing, Communications, and Applications (TOMM), 21 pps., <https://www.researchgate.net/publication/324765505_Learning_a_Multi-Concept_Video_Retrieval_Model_with_Multiple_Latent_Variables>.

Mell et al., "The NIST Definition of Cloud Computing", National Institute of Standards and Technology, U.S. Department of Commerce, NIST Special Publication 800-145, Sep. 2011, 7 pages.

Minaee et al., "Deep-Sentiment: Sentiment Analysis Using Ensemble of CNN and Bi-LSTM Models", 6 pps., Apr. 8, 2019, <https://arxiv.org/pdf/1904.04206.pdf>.

Loshin, "Data Standardization", in Master Data Management, 2009, ScienceDirect, 13 pps., <https://www.sciencedirect.com/topics/computer-science/data-standardization>.

Papacharissi, "A Networked Self Identity, Community, and Culture on Social Network Sites", 337 pps., First published 2011 by Routledge.

(56) References Cited

OTHER PUBLICATIONS

Purpura, "A Semi-Automated Approach for Information Extraction, Classification and Analysis of Unstructured Data", arXiv:1910.12734v1 [cs.IR] Oct. 20, 2019, 5 pps., <https://arxiv.org/abs/1910.12734>.

Ryan et al., "Wearable Sensor to Monitor COVID-19 Like Signs and Symptoms", US National Library of Medicine, ClinicalTrials.gov, Identifier: NCT04393558, first published Apr. 19, 2020, 7 pps., <https://clinicaltrials.gov/ct2/show/record/NCT04393558>.

Seyler et al., "Generating Quiz Questions from Knowledge Graphs", 2 pps, WWW 2015 Companion, May 18-22, 2015, Florence, Italy. ACM 978-1-4503-3473-0/15/05, <https://publish.illinois.edu/dominic-seyler/files/2019/03/www2015-final.pdf>.

Sidana, "Top Five Emotion / Sentiment Analysis APIs for understanding user sentiment trends.", May 20, 2017, Medium, 9 pps., <https://medium.com/sifium/top-five-emotional-sentiment-analysis-apis-116cd8d42055>.

Stejskal, "Empty Speech Pause Detection Algorithms' Comparison", Article in Journal of Advanced Computational Intelligence and Intelligent Informatics • Jan. 2011, 17 pps., <https://www.researchgate.net/publication/259470072_Empty_Speech_Pause_Detection_Algorithms'_Comparison>.

Tran et al., "Micro-expression spotting: A new benchmark", arXiv:2007.12421v2 [cs.CV] Dec. 28, 2020, 19 pps., <https://arxiv.org/abs/2007.12421>.

Van Edwards, "The Definitive Guide to Reading Microexpressions (Facial Expressions)", Science of People, 80 pps., printed from the Internet on Jun. 15, 2021, <https://www.scienceofpeople.com/microexpressions/>.

Zhang, "Understand Data Normalization in Machine Learning", Mar. 27, 2019, towards data science, 9 pps., <https://towardsdatascience.com/understand-data-normalization-in-machine-learning-8ff3062101f0>.

\* cited by examiner

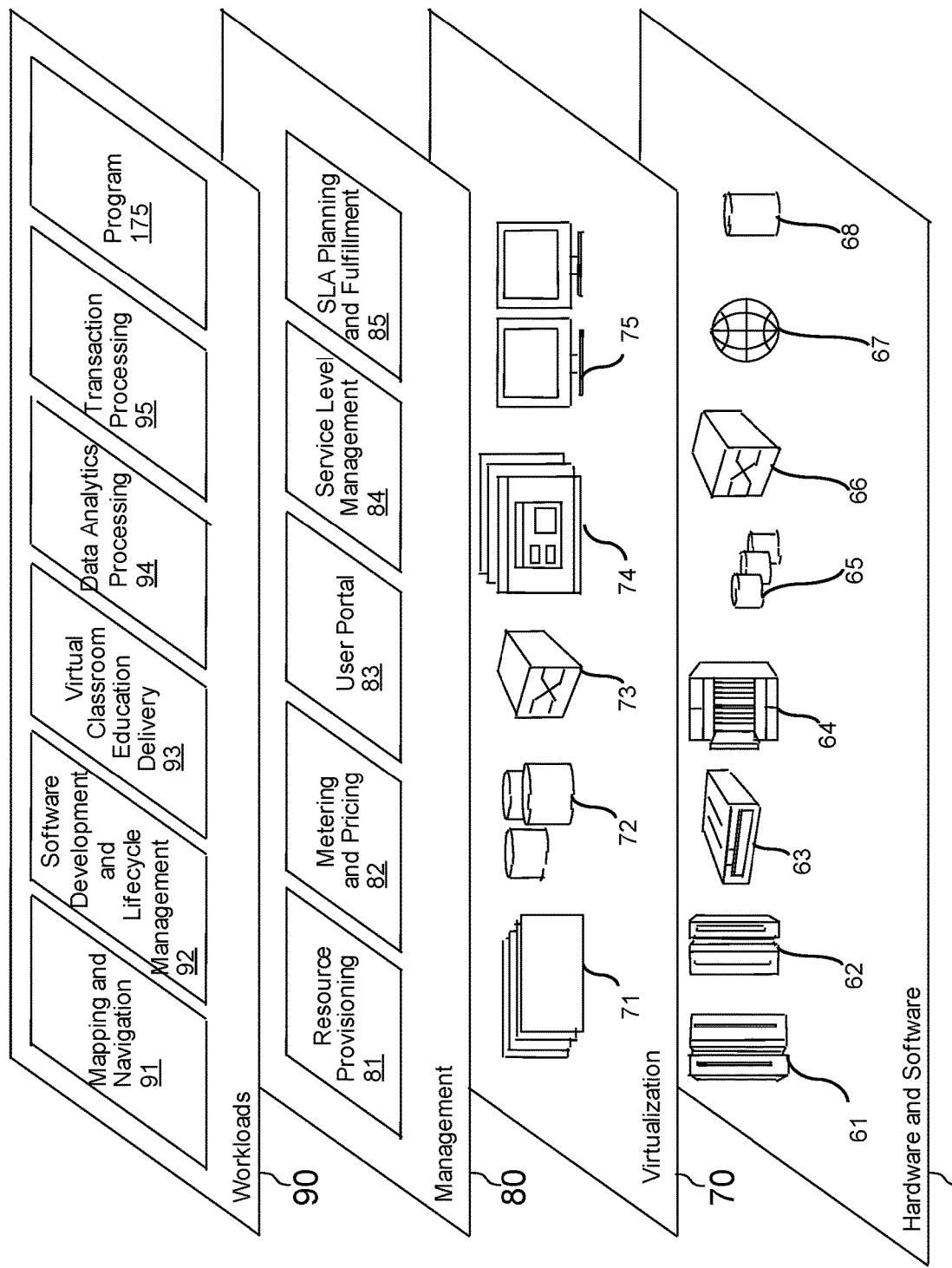

AUGMENTING USER RESPONSES TO QUERIES

FIELD OF THE INVENTION

The disclosure relates generally to the generating responses to queries. The disclosure relates particularly to automated generation of responses to augment user response to queries.

BACKGROUND

Wearable devices exist to provide data indicative of a user's current health. Such data includes, a user's heart rate, blood pressure, blood oxygen level, blood glucose level, and other user health condition data. Such data may be collected and tracked over time, providing an indication of changes in a user's medical condition.

Speech to text algorithms provide a means for converting digitized audio files to text files. Text to speech algorithms provide a means for converting digital text data to digitized audio data which can be played as audio from a speaker.

SUMMARY

The following presents a summary to provide a basic understanding of one or more embodiments of the disclosure. This summary is not intended to identify key or critical elements or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatuses and/or computer program products enable generating responses to queries.

Aspects of the invention disclose methods, systems and computer readable media associated with generating a query response by receiving data for a non-user utterance, determining a question answering (QA) system response to the non-user utterance, receiving data for a user utterance responsive to the non-user utterance, determining a confidence score for the user utterance, determining a deviation between the user utterance and the QA system response, and providing the QA system response according to a combination of the deviation and the confidence score.

BRIEF DESCRIPTION OF THE DRAWINGS

Through the more detailed description of some embodiments of the present disclosure in the accompanying drawings, the above and other objects, features and advantages of the present disclosure will become more apparent, wherein the same reference generally refers to the same components in the embodiments of the present disclosure.

FIG. 4 depicts abstraction model layers, according to an embodiment of the invention.

DETAILED DESCRIPTION

Figure 1:
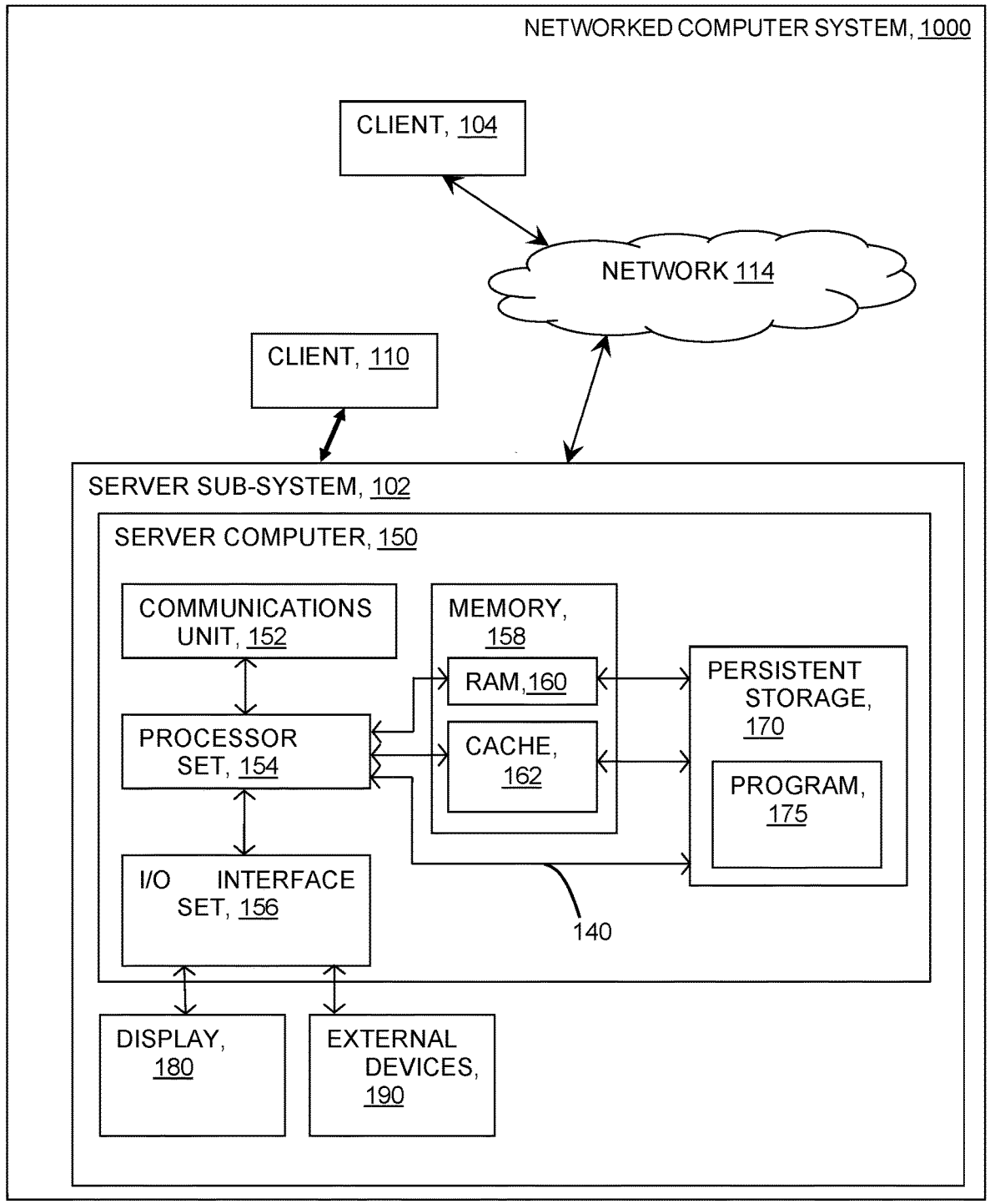
FIG. 1 provides a schematic illustration of a computing environment, according to an embodiment of the invention.

Some embodiments will be described in more detail with reference to the accompanying drawings, in which the embodiments of the present disclosure have been illustrated. However, the present disclosure can be implemented in various manners, and thus should not be construed to be limited to the embodiments disclosed herein.

In making a diagnosis and preparing a treatment plan according to that diagnosis, medical practitioners rely upon information received from the patient. Inaccuracies in the patient provided information may lead to a misdiagnosis and an incorrect treatment plan. The result of this may include incomplete or delayed patient recovery, or a complete lack of patient recovery from the current medical state. Patient's answer a practitioner's queries to the best of their ability but may not always present accurate response for a variety of reasons. Patients may not remember accurate answers or may not have been tracking their symptoms closely enough to provide accurate answers to queries such as "How many days have you had a fever?", or "How long have you had your current symptoms?". Disclosed embodiments combine data from wearable biometric sensors, image analysis and real-time patient-practitioner conversation analysis to determine that a patient lacks confidence in their answer to a query and that analysis of the patient's biometric data leads to a different answer.

Aspects of the present invention relate generally to question answering systems and, more particularly, to unsupervised dynamic confidence thresholding for answering questions. In embodiments, a question answering (QA) system receives a question from a user device, determines one or more answers for the question, returns the determined answers whose confidence score is greater than a confidence threshold, and does not return the determined answers whose confidence score is less than the confidence threshold. The system further receives a user response to the questions together with data indicative of the user's confidence in their own answer. The system analyzes the user response data to determine the user's confidence in the answer and compares the user's answer to answers generated by the system in response to the same question. According to aspects of the invention, in instances where the user's confidence is low, there is a difference between the user's answer and at least one answer generated by the system, and the user has opted in to automatic responses, the QA system automatically provides that system answer as an alternative to the user's answer. In this manner, implementations of the invention provide alternative answers offering higher levels of accuracy in response to queries posed to the user. System responses may be provided automatically under these conditions depending upon the opt-in status of the user. When the user has opted-in to automatic responses and when the system determines that the current query is non-sensitive in nature, the system automatically provides the generated response. For sensitive queries, the system provides the alternative answer to the user enabling the user to share the alternative answer with the originator of the query.

In accordance with aspects of the invention there is a method for automatically generating responses to queries made to a user. Embodiments convert a query to digital text data using speech to text programming and then process the digitized text suing a Natural language processing (NLP) algorithm to determine one or more intents included within the query. Embodiments provide the NLP output as an input to a QA system including a QA corpus. The QA system determines one or more responses to the input, each response includes an associated confidence level corresponding to the likelihood that the particular responses selected is the best response to the intent expressed in the query as embodied in the output of the NLP algorithm.

Aspects of the invention provide an improvement in the technical field of QA systems. Conventional QA systems utilize static matching databases or defined decision trees to determine an answer to a question posed to a user. In many cases, the predefined answers lack up to date information resulting in responses of little actual value to the questioner. Further, users in some settings, such as being questioned by a medical professional, may feel stressed and have difficulty interpreting questions and/or providing accurate responses. In some instances, a patient may be unable to provide answers due to the very conditions leading to efforts to seek treatment. Implementations of the invention leverage patient medical data provided by wearable sensors such that disclosed systems and methods provide the improvement of formulating accurate responses to health care provider questions, thereby enabling the desired user outcome of an accurate diagnosis and effective therapies for the patient/user.

Aspects of the invention also provide an improvement to computer functionality. In particular, implementations of the invention are directed to a specific improvement to the way QA systems operate, embodied in the continually adjusted patient medical data and history as well as monitoring a patient/user's confidence in a provided answer as well as differences between patient answers and system answers derived from up to date health data. In embodiments, the system adjusts the health profile of the user according to continuously captured biometric health data and monitors the user's responses to questions. Both the intent of the response and the user's confidence in the response are tracked and used in determining a system action. As a result of adjusting a user's health profile and monitoring user responses and associated confidence levels, the system increases the likelihood that the system and user will provide accurate answers to health questions in situations where user answers fail to provide accurate information to a questioner. In this manner, embodiments of the invention affect how the QA system functions (i.e., the likelihood of providing up to date and accurate answers to queries when a user fails to do so.

As an overview, a QA system is an artificial intelligence application executed on data processing hardware that answers questions pertaining to a given subject-matter domain presented in natural language. The QA system receives inputs from various sources including input over a network, a corpus of electronic documents or other data, data from a content creator, information from one or more content users, health data from one or more wearable sensors, user data from one or more cameras and/or microphones, and other such inputs from other possible sources of input. Collected data may further include textual health data of the user including named entity recognition data extracted using natural language understanding algorithms. Data may also include environmental data such as user's locations, and temperature, barometric pressure, air quality, humidity, etc., of the user's surroundings. Environmental data may further include the user's proximity to contagious individuals identified anonymously by the system as other system participants, or the location of the user in or near an afflicted area having a known high rate of incidence of a particular disease or conditions associated with particular diseases. Data may also include time durations which the user has spent in close proximity to afflicted individuals. Data may further user food intake data provided by a user through a user interface to the system resident upon the user's device such as a computer, tablet computer or smartphone. Data storage devices store the corpus of data. A content creator creates content in a document for use as part of a corpus of data with the QA system. The document may include any file, text, article, or source of data for use in the QA system. For example, a QA system accesses a body of knowledge about the domain, or subject matter area (e.g., financial domain, medical domain, legal domain, etc.) where the body of knowledge (knowledgebase) can be organized in a variety of configurations, such as but not limited to a structured repository of domain-specific information, such as ontologies, or unstructured data related to the domain, or a collection of natural language documents about the domain.

In an embodiment, the method standardizes and normalizes the received user data from wearable sensors and other sources described above. The standardized and normalized data is then ingested by the system and analyzed to extract a body of useful information related to the current domain of the method (e.g., health information queries). The system stores the data and augments the stored body of data as the system receives additional user data. The system utilizes the stored data to build a knowledge graph, decision tree, matching database or other QA decision structure incorporating the data, for generating responses to queries.

Disclosed embodiments are discussed in terms of a conversation between a user and health care provider as a non-limiting example. Disclosed embodiments may also be applicable to conversations between a user and any service provider by appropriately expanding the corpus of the system to include such things as a user's financial records or private data.

In an embodiment, one or more components of the system can employ hardware and/or software to solve problems that are highly technical in nature (e.g., receiving data associated with a non-user utterance, determining an intent of the non-user utterance using natural language processing or similar methods, determining a system response to the non-user utterance according to the intent, receiving data associated with a user response to the non-user utterance, determining a confidence score associated with the user response, determining a deviation between the user response and the system response, providing the system response according to the deviation between the user response and the system response and the confidence level, etc.). These solutions are not abstract and cannot be performed as a set of mental acts by a human due to the processing capabilities needed to facilitate augmenting user query responses, for example. Further, some of the processes performed may be performed by a specialized computer for carrying out defined tasks related to providing responses to queries. For example, a specialized computer can be employed to carry out tasks related to assisting a user in responding to a query or the like.

In an embodiment, a method for augmenting a user's responses to queries includes receiving data associated with or corresponding to a non-user utterance. The non-user may have asked the user a question, either orally, or in a written form, such as via an SMS text message communicated over a telecommunications network. In this embodiment, the method receives the non-user utterance data and processes the data. Processing of oral communications data includes speech-to-text processing. The method translates a digital audio data file derived from the oral communication to a string of phonemes corresponding to the spoken words of the original speech. The speech-to-text algorithm then translates the string of phonemes to a string of words, the digitized text output of the algorithm.

In an embodiment, the method passes the text derived from the oral communications, or the text received directly, to a natural language processing (NLP) algorithm to determine one or more intents associated with the text.

In an embodiment, the method further analyses the audio data for the non-user utterance to derive a non-user confidence level according to an attribute such as tonal analysis of the data. In an embodiment, the method further analyzes the non-user utterance using attributes including pause gap analysis, personality trait analysis, and facial expression analysis of images of the non-user during the utterance and ongoing conversation with the user. These analyses provides an indication of the confidence of the non-user in their utterance. For example, the confidence of a health care provider in their diagnosis. In this embodiment, the method uses a function combining the attributes such as tonal analysis output, the facial expression output, personality trait analysis output, and the pause gap analysis combined with weighting coefficients for each of the values, to determine an overall confidence value for the utterance. In an embodiment, the method uses a long short-term memory neural network (LSTM), or similar architecture, to classify the confidence value for the utterance. In training the LSTM model, the method initializes the weights using random values. The method then adjusts the weights using back-propagation and labeled data derived from interactions between the non-user and the QA system. Over time and the course of a plurality of interactions, the weights are trained and calibrated to fit the personality traits and communication style of the non-user.

Disclosed embodiments can perform natural language processing (NLP) for extraction of NLP output parameter values from received voice data of user, as well as prompting data from a VA. Embodiments may perform one or more of: a topic classification process that determines topics of messages and outputs one or more topic NLP output parameter value, a sentiment analysis process which determines sentiment parameter value for a message, e.g., polar sentiment NLP output parameters, "negative," "positive," and/or non-polar NLP output sentiment parameters, e.g., "anger," "disgust," "fear," "joy," and/or "sadness" or other classification process for output of one or more other NLP output parameter values, e.g., one or more "social tendency" NLP output parameter, related to personality traits of a speaker, or one or more "writing style" NLP output parameter, and/or one or more part of speech NLP output parameter value. Part-of-speech tagging methodologies can include use of, e.g., Constraint Grammar, Brill tagger, Baum-Welch algorithm (the forward-backward algorithm) and the Viterbi algorithm which can employ use of the Hidden Markov models. Hidden Markov models can be implemented using the Viterbi algorithm. The Brill tagger can learn a set of rule patterns and can apply those patterns rather than optimizing a statistical quantity. Applying natural language processing can also include performing sentence segmentation which can include determining where a sentence ends, including, e.g., searching for periods, while accounting for periods that designate abbreviations.

Disclosed embodiments performing natural language processing can include performing (a) topic classification and output of one or more topic NLP output parameter for a received message, (b) sentiment classification and output of one or more sentiment NLP output parameter value for a received message, or (c) other NLP classifications and output of one or more other NLP output parameter for the received message. Topic analysis for topic classification and output of NLP output parameter values can include topic segmentation to identify several topics within a message. Topic analysis can apply a variety of technologies, e.g., one or more of hidden Markov model (HMM), artificial chains, passage similarities using word co-occurrence, topic modeling, or clustering. Sentiment analysis for sentiment classification and output of one or more sentiment NLP parameter can determine the attitude of a speaker or a writer with respect to some topic or the overall contextual polarity of a document. The attitude may be the author's judgment or evaluation, affective state (the emotional state of the author when writing), or the intended emotional communication (emotional effect the author wishes to have on the reader). In one embodiment, sentiment analysis can classify the polarity of a given text as to whether an expressed opinion is positive, negative, or neutral. Advanced sentiment classification can classify beyond a polarity of a given text. Advanced sentiment classification can classify emotional states as sentiment classifications. Sentiment classifications can include the classification of "anger," "disgust," "fear," "joy," and "sadness." Such classification results include a vector associated with the non-user utterance and a confidence value associated with each classification.

In this embodiment, the method provides the output of the NLP as an input to a question answering (QA) system. The QA system includes a matching database, decision tree, or knowledge graph, constructed using a provided corpus of knowledge relating to the specific domain the system and method are directed toward. For example, financial information, medical and/or health information, etc. For the example of health and medical applications, the corpus includes biometric health data collected from one or more wearable sensors worn by the current system user. Exemplary wearable sensors include blood pressure monitors, heart rate and blood oxygen monitors, blood glucose monitors, body temperature, etc. For this example, the method and system track wearable generated data over time and monitor trends in the provided data as well as deviations from normal over the monitoring time period. In this embodiment, the system and method track data in comparison to normal for the user as well as normal in a broader sense, such as normal for an adult male, aged fifty-five. In this embodiment, the method maintains and updates a database of user data as well as a database of normal data values for demographic groups relevant to the user. Such data bases may be maintained on a local computing device for the user or may be maintained on edge cloud or cloud resources to provide additional storage and computing resources.

In an embodiment, the method analyzes user health data from the wearable(s) and predicts non-user queries according to the current trends in the health data. In this embodiment, the method utilizes available medical diagnosis expert systems in the evaluation of the health data. The method determines a predicted diagnosis of the user's current state and generates precited questions associated with the predicted diagnosis, as well as an order of progression for the set of predicted questions. For each predicted diagnosis, the method generates a confidence score based upon the likelihood that the predicted diagnosis is accurate. As an example, the method analyzes the health data using a machine learning classification model and determines a confidence associated with respective differing diagnosis arising the classification based upon the health data. In this embodiment, the method uses a machine learning classification model such as a convolutional neural network, a recurrent neural network, a generative adversarial network, a variational autoencoder, a long short-term memory model, or other classification models to analyze the health data of the user. In an embodiment, training such a model includes providing the model with labeled health data associated with known diagnoses and using back propagation to derive appropriate network node weights for the model. The method dynamically generates response to the predicted question using the QA system and the current health data and data trends. In one embodiment, the system collects additional health data according to a predicted diagnosis. The system collects additional health data to corroborate or refute the predicted diagnosis.

In an embodiment, the user opts-in to social media analysis by the system and provides data relevant for system access to the user's social media accounts. In this embodiment, the system analyzes the social media accounts of the user to evaluate the user's mental health and current physical activities. Further analysis provides the method with indications as to the personality traits and normal communications styles of the user in varying situations. These indications serve as inputs in determining the user's confidence is their responses to queries.

In an embodiment, the method analyzes images gathered from system or user device cameras. The analysis included comparisons in images taken over time to evaluate changes associated with aberrations in a user's appearance or other changes, such as a wound healing or a rash changing. In an embodiment, the analysis further includes facial expression analysis of the user during conversations. Facial expression analysis serves as an input to confidence score determinations.

In an embodiment, the method provides the most recent intent derived by the NLP from the non-user utterance data to the QA system. In an embodiment, the method provides the on-going string of intents associated with non-user utterances from a conversation between the user and the non-user to the QA system. In this embodiment, the QA system analyzes the intent or series of intents and determines an output response to the most recent intent, either alone or in the context of the string of intents from the conversation. In one embodiment, the response includes health data relevant to the input intent and the response. The response output from the QA system includes a vector representation of the response. The QA system provides a confidence score for one or more responses to the query, either as part of the vector representation of the response or as a separate value.

In an embodiment, the system utilizes Lambda processing architecture processing historic health data and health information to generate a diagnosis and predict questions for a health care provider as a batch process, then uses a speed layer process to evaluate real-time non-user queries and user responses using the developed QA response generating system.

The method and system monitor the user and effectively listen or otherwise receive the user's response to the non-user utterance. The system may utilize a microphone of a user's device or system computing device to capture audio of a user response, or the system may monitor an electronic text conversation between the user and on-user to capture the user's text-based response to a text-based non-user query.

Similarly, to the non-user utterance, the method and system process user response audio data using speech-to-text to yield digitized text data from the user audio or translate a user's text response to digitized text data. In an embodiment, the method processes the user response data using NLP to generate a vector representation of the user's response. In embodiment, the method and system utilize tonal analysis, pause gap analysis, personality trait analysis, and facial expression analysis, of user audio data and image data, to determine a user confidence value for the user's response. The confidence value represents the level of confidence of the user that the user provided response is accurate and complete.

In this embodiment, the method uses a function combining the tonal analysis output, the facial expression output, personality analysis, and the pause gap analysis combined with weighting coefficients for each of the values, to determine an overall confidence value for the utterance. In an embodiment, the method uses a long short-term memory neural network (LSTM), or similar architecture, to classify the confidence value for the utterance. In training the LSTM model, the method initializes the weights using random values. The method then adjusts the weights using back-propagation and labeled data derived from interactions between the user and the QA system and optionally labeled data from the user's social media and other communication outlets. Over time and the course of a plurality of interactions, the weights are trained and calibrated to fit the personality traits and communication style of the user.

In an embodiment, the method compares the vector associated with the system's generated response to the non-user query with the vector for the user's response to the same query. In this embodiment, the method determines a similarity and deviation between the two vectors. Examples of methods of determining the similarity of text-based documents include Jaccard distance, Cosine distance, Euclidean distance, Relaxed Word Mover's Distance, and may utilize term frequency-inverse document frequency (tf-idf) techniques. A person of ordinary skill in the art may apply other techniques of determining similarity between page pairings of a document other than those presented, herein, and not deviate from, or limit the features of embodiments of the present invention.

In an embodiment, the method uses a combination of the user's confidence score and the degree of deviation between the response vectors to determine the method's action relating to the generated response. When a deviation between the response vectors plus the inverse of the score of user confidence exceeds a defined threshold, the method next considers user preferences regarding the next action. The method considers the inverse of the user's confidence score in combining the factors such that a low user confidence increases the likelihood of a system interjection while a high user confidence decreases the likelihood of an interjection.

A user may opt-in to automated responses wherein the system interjects the generated response into the ongoing conversation. In an embodiment, the system asks for confirmation from the user before proceeding to interject. A user may choose to opt-out of automatic interjection of responses. In this case the system detects that the combination of user confidence and response vector deviation exceeds the defined threshold and may then provide the user with the generated response, enabling the user to choose whether or not to provide the generated response. In this embodiment, the system may provide the generated response to the user using a text message to the user's device such as a smartphone. In an embodiment, the system may provide the user an option to enable the system to continue the conversation with the non-user based upon generated responses derived using the biometric data embedded in the knowledge graph of the QA system.

In an embodiment, the method further considers the non-user confidence as well as the user confidence and the response deviation in determining the system's next action. As an example, the method may reduce a weighting associated with the response deviation for instances where the predicted diagnosis differs from non-suer's diagnosis and the non-user's confidence level is high, e.g., exceeding 90%. In an embodiment, the method compares the non-user confidence score and the confidence score associated with the generated system response and system diagnosis in determining the next system action. System confidence scores higher than non-user confidence scores weigh toward providing the system generated response while non-user confidence scores higher than system generated response confidence scores weigh toward not providing the generated response to the user.

In an embodiment, the system determines that the combination of user confidence and response vector deviation exceeds the defined threshold and offers the user a set of recommendations/actions such as: suggesting the user provide the generated response to the non-user, suggesting that the system converse with the non-user to provide the generated response, suggesting the system take over the conversation and provide the generated response as well as additional supporting data to the non-user.

In an embodiment, the method considers the context of the communication in determining a next system action. For example, the method considers the nature of the conversation—e.g., in-person, telemedicine visit, text-only conversation, etc., in determining whether the system should interject directly or provide generated response to the user.

In an embodiment, the method considers the sensitivity of the non-user query in determining a next system action. For queries relating to sensitive health matters, the system may provide the generated response to the user rather than interjecting the response directly into the conversation. In this embodiment, the method avoids providing audible responses which include potentially sensitive user health information, which responses may be overheard. In this embodiment, the method uses the NLP generated vectors for the non-user utterance, the system generated response and the user response utterance, in determining query sensitivity.

In an embodiment, the method provides the generated responses using text to speech programming wherein the generated responses are provided as a synthesized string of phonemes enabling an audible response from the system when enabled by the user. In this embodiment, the method provides the text-to-speech data to the user's device such as a smartphone.

FIG. 1 provides a schematic illustration of exemplary network resources associated with practicing the disclosed inventions. The inventions may be practiced in the processors of any of the disclosed elements which process an instruction stream. As shown in the figure, a networked Client device 110 connects wirelessly to server sub-system 102. Client device 104 connects wirelessly to server sub-system 102 via network 114. Client devices 104 and 110 comprise response generation program (not shown) together with sufficient computing resource (processor, memory, network communications hardware) to execute the program. In an embodiment, client devices 104 and 110 constitute user access points for the response generation program, providing user interfaces to enable receipt of utterance data and the provision of generated response outputs to the user. As shown in FIG. 1, server sub-system 102 comprises a server computer 150. FIG. 1 depicts a block diagram of components of server computer 150 within a networked computer system 1000, in accordance with an embodiment of the present invention. It should be appreciated that FIG. 1 provides only an illustration of one implementation and does not imply any limitations with regard to the environments in which different embodiments can be implemented. Many modifications to the depicted environment can be made.

Server computer 150 can include processor(s) 154, memory 158, persistent storage 170, communications unit 152, input/output (I/O) interface(s) 156 and communications fabric 140. Communications fabric 140 provides communications between cache 162, memory 158, persistent storage 170, communications unit 152, and input/output (I/O) interface(s) 156. Communications fabric 140 can be implemented with any architecture designed for passing data and/or control information between processors (such as microprocessors, communications, and network processors, etc.), system memory, peripheral devices, and any other hardware components within a system. For example, communications fabric 140 can be implemented with one or more buses.

Memory 158 and persistent storage 170 are computer readable storage media. In this embodiment, memory 158 includes random access memory (RAM) 160. In general, memory 158 can include any suitable volatile or non-volatile computer readable storage media. Cache 162 is a fast memory that enhances the performance of processor(s) 154 by holding recently accessed data, and data near recently accessed data, from memory 158.

Program instructions and data used to practice embodiments of the present invention, e.g., the response generating program 175, are stored in persistent storage 170 for execution and/or access by one or more of the respective processor(s) 154 of server computer 150 via cache 162. In this embodiment, persistent storage 170 includes a magnetic hard disk drive. Alternatively, or in addition to a magnetic hard disk drive, persistent storage 170 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 170 may also be removable. For example, a removable hard drive may be used for persistent storage 170. Other examples include optical and magnetic disks, thumb drives, and smart cards that are inserted into a drive for transfer onto another computer readable storage medium that is also part of persistent storage 170.

Communications unit 152, in these examples, provides for communications with other data processing systems or devices, including resources of client computing devices 104, and 110. In these examples, communications unit 152 includes one or more network interface cards. Communications unit 152 may provide communications through the use of either or both physical and wireless communications links. Software distribution programs, and other programs and data used for implementation of the present invention, may be downloaded to persistent storage 170 of server computer 150 through communications unit 152.

I/O interface(s) 156 allows for input and output of data with other devices that may be connected to server computer 150. For example, I/O interface(s) 156 may provide a connection to external device(s) 190 such as a keyboard, a keypad, a touch screen, a microphone, a digital camera, and/or some other suitable input device. External device(s) 190 can also include portable computer readable storage media such as, for example, thumb drives, portable optical or magnetic disks, and memory cards. Software and data used to practice embodiments of the present invention, e.g., response generating program 175 on server computer 150, can be stored on such portable computer readable storage media and can be loaded onto persistent storage 170 via I/O interface(s) 156. I/O interface(s) 156 also connect to a display 180.

Display 180 provides a mechanism to display data to a user and may be, for example, a computer monitor. Display 180 can also function as a touch screen, such as a display of a tablet computer.

Figure 2:
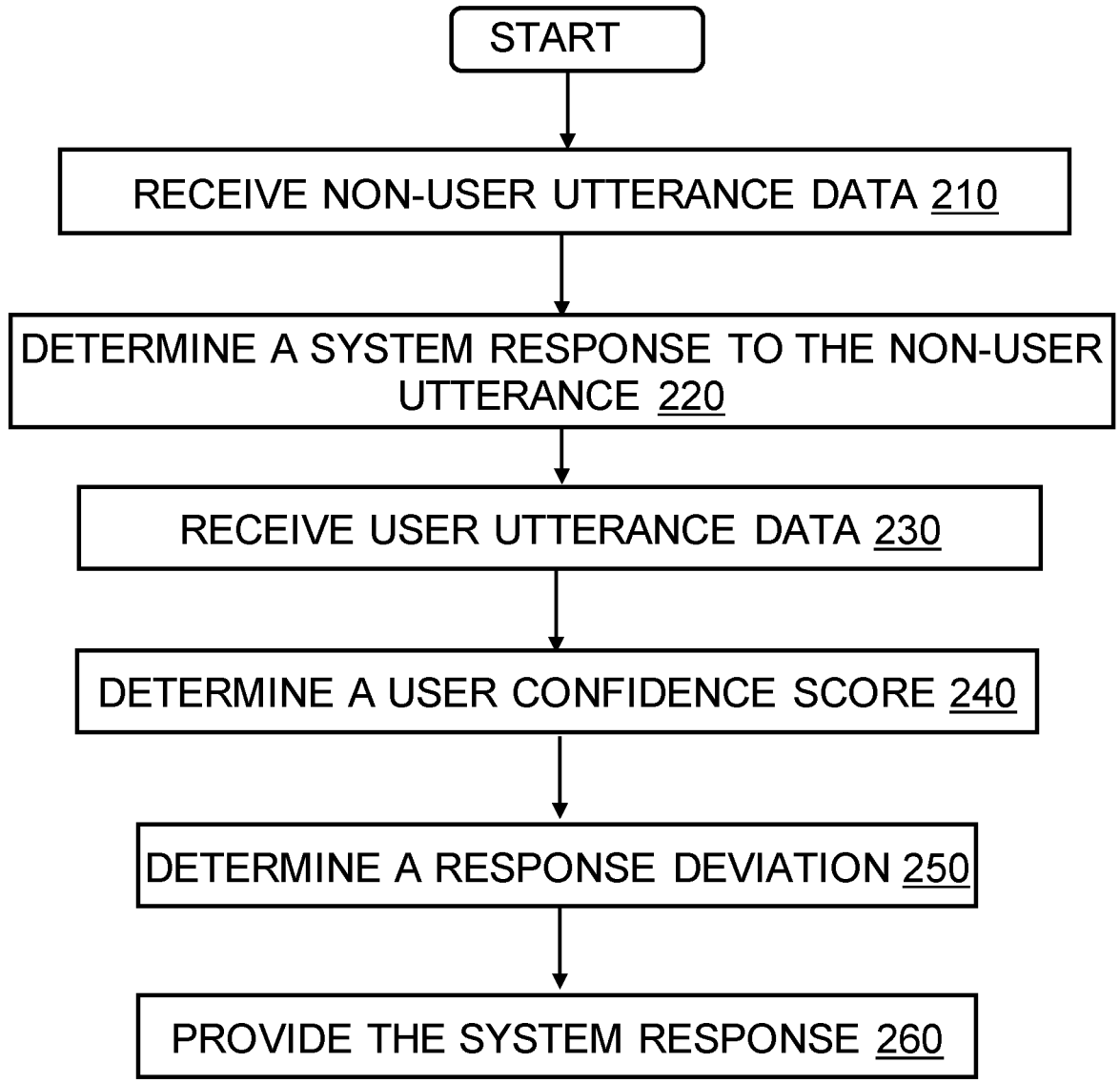
FIG. 2 provides a flowchart depicting an operational sequence, according to an embodiment of the invention.

FIG. 2 provides a flowchart 200, illustrating exemplary activities associated with the practice of the disclosure. After program start, at block 210, response generating program 175, receives data associated with a non-user utterance. The data may include audio data, text data, or a combination of audio and text data. In an embodiment, the method processes audio data using speech to text programming. The method processes the data suing NLP programming yielding one or more intents from the data. In an embodiment, the method further processes the audio data to determine a non-user confidence score for the non-user utterance using tonal analysis, pause gap analysis. In an embodiment, the method analyzes images of the non-user during the conversation using facial expression analysis to support the confidence score determination.

At block 220, the method of response generating program 175 determines a response to the non-user utterance using a QA system and knowledge corpus embodied in a decision tree, knowledge graph, or other QA structure. In an embodiment, the QA structure includes decisions nodes or comparable structures associated with biometric data received from one or more wearable sensors. The method receives the intent of the non-user utterance from the NLP and processes the intent—or string of recent intents—to determine the system response to the non-user utterance. In an embodiment, the method processes the generated response using NLP and determines a vector representation and confidence score for the generated response.

At block 230, the method of response generating program 175 receives data associated with a user response to the non-user utterance. This data may be audio data, text data, or a combination of audio and text data. For audio data the system and method use speech-to-text processing to convert the audio data to text data for further processing. The method processes the text data using NLP to generate a vector representation of the user response data.

At block 240, the method of response generating program 175 further processes data, including user response audio data and user image data, to determine a user confidence score for the user response. The confidence score includes tonal analysis, pause gap analysis of the user response, personality trait analysis, and facial cue analysis of the user images captured during the response. In an embodiment, the method uses a trained LSTM model to determine the user confidence score from the audio and image data.

At block 250, the method determines a deviation between the vector representation of the system response and the vector representation of the user response. The method may use cosine similarity or similar methods to determine the deviation between the vectors.

At block 260, the method determines a system action to be taken, such as providing the system response to the non-user utterance. The system combines the user confidence score and the response vector deviation to determine if the system response should be provided to the user, interjected into the conversation, or both. The user may opt-in to having the system automatically interject the system response when the user confidence is low and the vector deviation is high, or to have the system prompt the user for guidance in such circumstances. The user may enable the system to take over the conversation with the non-user under such circumstances, enabling the system to provide the non-user with additional information subject to non-user queries, or subject to a determination of relevance of the additional information by the system. The system considers the user's opt-in status in determining a next action to take.

In an exemplary embodiment, a user registers for the disclosed service and receives a unique user identification. The user account is registered and all information collected from that point in time will be stored in a private cloud associated with the user's account and identification. The user may opt-in to allowing the system access to the collected information. The user's wearable sensor(s) are associated with the account and the method captures all data gathered by the sensor(s) and stores the data in the private cloud. In an embodiment, the method standardizes, normalizes and stores the incoming user data, including biometric sensor data, health history data, etc., the method extracts information from the data and generates a knowledge graph, decision tree or other QA system architecture from the data.

In this embodiment, a user begins to experience a low-grade fever on a Thursday, as recorded by the system tracking data from a body temperature sensor worn by the user. The user is unaware of their condition. The fever persists through the weekend. By Monday the user's condition has worsened, leading them to schedule an appointment with their physician. At the physician's office on Monday afternoon, their Doctor asks how long they have been feeling ill.

The system processes the Doctor's question and the QA portion of the system generates answers including "I have had a low-grade fever since last Thursday" from the NLP intent extracted from the Doctor's question and the tracked biometric data from the wearable sensor. The user responds, "I started to feel sick yesterday." The system processes the user's response using NLP and determines the user's confidence score for the response from tonal analysis, pause gap analysis and facial expression analysis combined with a user personality trait analysis. The determined confidence score is high as the user is unaware of the timing of the onset and the duration of their symptoms. The system determines a large deviation between the user's response and the system generated answer supported by the biometric data from the wearable sensor. The system prompts the user with the generated response "I have had a low-grade fever since last Thursday" and enables the user to choose whether to provide their Doctor with this response according to the opt-in status of the user. The user provides the generated response and opts-in to allowing the system to share data directly with the Doctor.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 3:
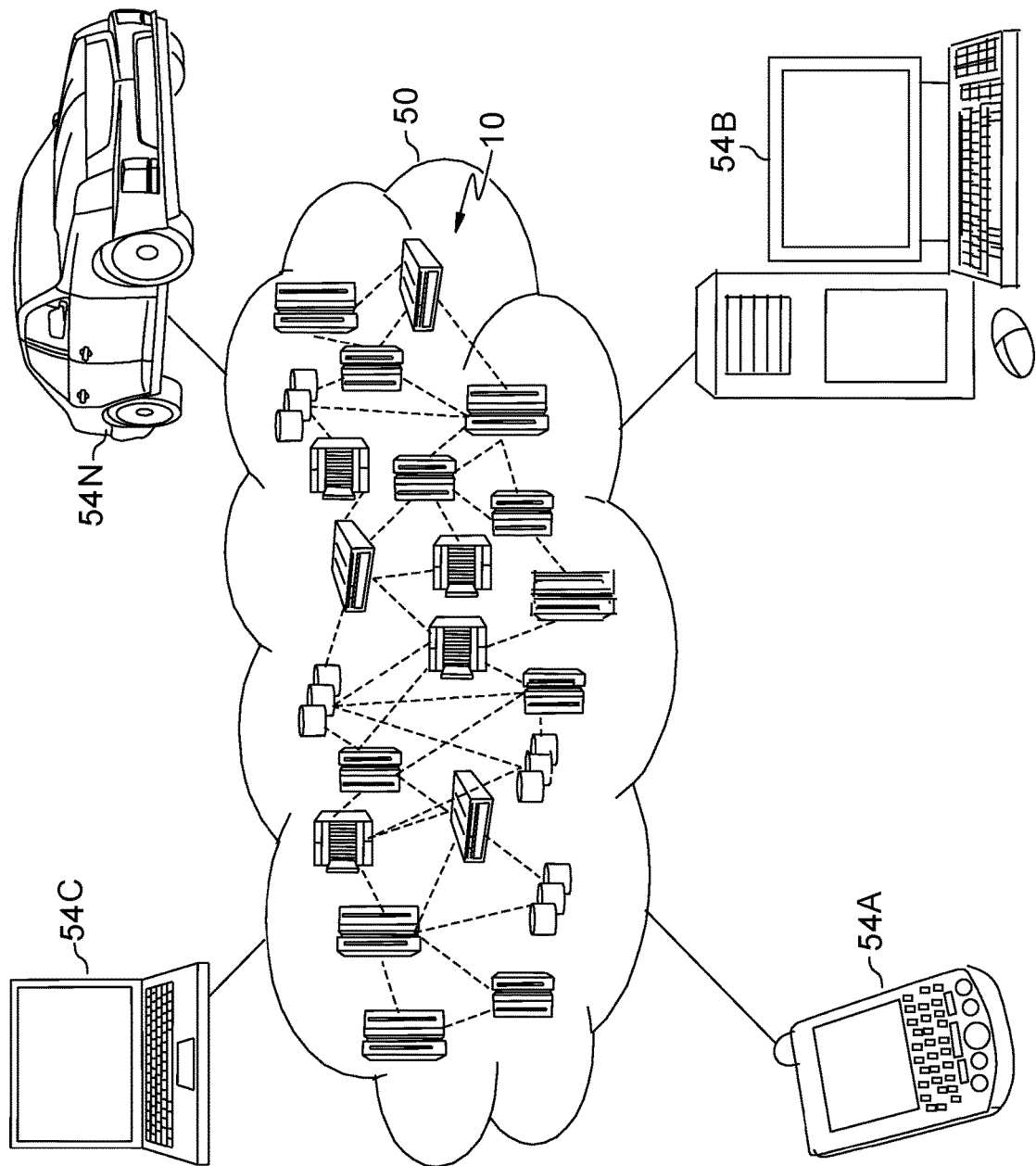
FIG. 3 depicts a cloud computing environment, according to an embodiment of the invention.

Referring now to FIG. 3, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 3 are intended to be illustrative only and that computing nodes 10 and cloud computing environment 50 can communicate with any type of computerized device over any type of network and/or network addressable connection (e.g., using a web browser).

Referring now to FIG. 4, a set of functional abstraction layers provided by cloud computing environment 50 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture-based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and response generating program 175.

The present invention may be a system, a method, and/or a computer program product at any possible technical detail level of integration. The invention may be beneficially practiced in any system, single or parallel, which processes an instruction stream. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, or computer readable storage device, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions collectively stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method for generating a query response, the method comprising:
receiving, by one or more computer processors, data for an utterance;
determining, by the one or more computer processors, a first vector representation for a question answering system response to the utterance;
receiving, by the one or more computer processors, data for a user utterance responsive to the utterance;
determining, by the one or more computer processors, a second vector representation and a confidence score for the user utterance;
determining, by the one or more computer processors, a deviation between the first vector representation and the second vector representation; and
providing, by the one or more computer processors, the question answering system response according to a communication context factor and a combination of the deviation and the confidence score.

2. The method according to claim 1, further comprising training, by the one or more computer processors, the question answering system by:
receiving user biometric data; and
building a knowledge graph incorporating the user biometric data.

3. The method according to claim 1, further comprising providing, by the one or more computer processors, the question answering system response to an originator of the utterance.

4. The method according to claim 1, wherein determining the confidence score includes consideration of an attribute selected from the group consisting of pause gap analysis, tonal analysis, facial expression analysis, personality trait analysis, and combinations thereof.

5. The method according to claim 1, further comprising providing, by the one or more computer processors, the question answering system response to the user according to a response sensitivity.

6. The method according to claim 1, further comprising providing, by the one or more computer processors, the question answering system response according to a user opt-in status.

7. A computer program product for generating a query response, the computer program product comprising one or more computer readable storage devices and collectively stored program instructions on the one or more computer readable storage devices, the stored program instructions comprising:
program instructions to receive data for an utterance;
program instructions to determine a first vector representation for a question answering system response to the utterance;
program instructions to receive data for a user utterance responsive to the utterance;
program instructions to determine a second vector representation and a confidence score for the user utterance;
program instructions to determine a deviation between the first vector representation and the second vector representation; and
program instructions to provide the question answering system response according to a communication context factor and a combination of the deviation and the confidence score.

8. The computer program product according to claim 7, the stored program instructions further comprising program instructions to train the question answering system by:
receiving user biometric data; and
building a knowledge graph incorporating the user biometric data.

9. The computer program product according to claim 7, the stored program instructions further comprising program instructions to provide the question answering system response to an originator of the utterance.

10. The computer program product according to claim 7, wherein determining the confidence score includes consideration of an attribute selected from the group consisting of pause gap analysis, tonal analysis, facial expression analysis, personality trait analysis, and combinations thereof.

11. The computer program product according to claim 7, the stored program instructions further comprising program instructions to provide the question answering system response to the user according to a response sensitivity.

12. The computer program product according to claim 7, the stored program instructions further comprising program instructions to provide the question answering system response according to a user opt-in status.

13. A computer system for generating a query response, the computer system comprising:
one or more computer processors;
one or more computer readable storage devices; and
stored program instructions on the one or more computer readable storage devices for execution by the one or more computer processors, the stored program instructions comprising:
program instructions to receive data for an utterance;
program instructions to determine a first vector representation for a question answering system response to the utterance;
program instructions to receive data for a user utterance responsive to the utterance;
program instructions to determine a second vector representation and a confidence score for the user utterance;
program instructions to determine a deviation between the first vector representation and the second vector representation; and
program instructions to provide the question answering system response according to a communication context factor and a combination of the deviation and the confidence score.

14. The computer system according to claim 13, the stored program instructions further comprising program instructions to train the question answering system by:
receiving user biometric data; and
building a knowledge graph incorporating the user biometric data.

15. The computer system according to claim 13, the stored program instructions further comprising program instructions to provide the question answering system response to an originator of the utterance.

16. The computer system according to claim 13, wherein determining the confidence score includes consideration of an attribute selected from the group consisting of pause gap analysis, tonal analysis, facial expression analysis, personality trait analysis, and combinations thereof.

17. The computer system according to claim 13, the stored program instructions further comprising program instructions to provide the question answering system response to the user according to a response sensitivity.

18. The computer system according to claim 13, the stored program instructions further comprising program instructions to provide the question answering system response according to a user opt-in status.

* * * * *